US008230998B2

(12) United States Patent  (10) Patent No.: US 8,230,998 B2
Boldra et al.  (45) Date of Patent: Jul. 31, 2012

(54) ABSORBENT PRODUCT STACKER PACKAGE

(75) Inventors: James A. Boldra, Menasha, WI (US); Jane L. Clough, Neenah, WI (US); Edward J. Foley, Greenville, WI (US); Keith R. Haen, Neenah, WI (US); Linda K. Lemerande, Waupaca, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 44 days.

(21) Appl. No.: 12/883,962

(22) Filed: Sep. 16, 2010

(65) Prior Publication Data

US 2011/0062042 A1    Mar. 17, 2011

Related U.S. Application Data

(62) Division of application No. 11/021,318, filed on Dec. 22, 2004, now abandoned.

(51) Int. Cl.
*B65D 73/00*    (2006.01)
(52) U.S. Cl. ........... 206/440; 206/494; 383/66; 383/203
(58) Field of Classification Search ................. 206/440, 206/441, 494, 812; 383/10, 66, 203–208
See application file for complete search history.

(56) References Cited

U.S. PATENT DOCUMENTS

| | | | |
|---|---|---|---|
| 4,076,663 A | 2/1978 | Masuda et al. | |
| 4,286,082 A | 8/1981 | Tsubakimoto et al. | |
| 4,798,603 A | 1/1989 | Meyer et al. | |
| 4,877,336 A | 10/1989 | Peppiatt | |
| 5,048,687 A | 9/1991 | Suzuki et al. | |
| 5,226,992 A | 7/1993 | Morman | |
| 5,282,687 A | 2/1994 | Yee | |
| 5,361,905 A * | 11/1994 | McQueeny et al. | 206/494 |
| 5,427,245 A | 6/1995 | Roussel | |
| 5,464,285 A * | 11/1995 | Anderson | 383/10 |
| 6,264,641 B1 | 7/2001 | Van Gompel et al. | |
| 6,293,443 B1 | 9/2001 | Nykoluk | |
| 6,296,094 B1 | 10/2001 | Knecht | |
| 6,439,386 B1 | 8/2002 | Sauer et al. | |
| 6,491,165 B2 | 12/2002 | Kuske et al. | |
| 6,523,653 B2 | 2/2003 | Roegner | |
| 6,698,928 B2 * | 3/2004 | Miller | 383/205 |
| 6,880,704 B2 * | 4/2005 | Bredahl | 206/494 |
| 2003/0115837 A1 * | 6/2003 | Zimmer et al. | 53/436 |
| 2004/0091184 A1 | 5/2004 | Miller | |
| 2006/0144736 A1 | 7/2006 | Goodrich et al. | |

FOREIGN PATENT DOCUMENTS

| | | |
|---|---|---|
| DE | 91 09 154 U1 | 10/1991 |
| EP | 0 539 703 A1 | 5/1993 |
| EP | 0 697 827 B1 | 5/2002 |
| JP | 2002-034767 A | 2/2002 |

* cited by examiner

*Primary Examiner* — Luan K Bui
(74) *Attorney, Agent, or Firm* — R. Joseph Foster, III

(57) ABSTRACT

A flexible packaging bags for containing and dispensing articles. More particularly, the present invention relates to a flexible packaging bag having a hanging element, permitting hanging of the bag after the bag has been initially opened.

6 Claims, 7 Drawing Sheets

ABSORBENT PRODUCT STACKER PACKAGE

This application is a divisional of application Ser. No. 11/021,318 entitled "ABSORBENT PRODUCT STACKER PACKAGE" and filed in the U.S. Patent and Trademark Office on Dec. 22, 2004 now abandoned.

BACKGROUND OF THE INVENTION

The present invention relates to flexible packaging bags for containing and dispensing articles. More particularly, the present invention relates to a flexible packaging bag having a hanger, permitting hanging of the bag after the bag has been initially opened.

Packaging bags composed of flexible polymer materials have been used for packaging various types of products, such as infant diapers, training pants, feminine care products, changing pads and adult incontinence garments. These bags allow packaging of the articles to create a carton-like look and a configuration facilitating transportation and display on retail shelves. The bag may include mechanisms for providing an access opening in the package.

Upon opening, many consumers place the open bag either in a closet or in a drawer, and remove a few articles to be placed next to a changing table or crib. This creates the situation where diapers may be located in two locations. This may also cause problems with handling and storage of loose diapers.

Accordingly, there remains a need for packaging bags that allow a user to hang a package in an easy and convenient way.

SUMMARY OF THE INVENTION

The present inventors undertook intensive research and development efforts concerning flexible packaging. While conducting their research, the present inventors discovered unique flexible packaging adapted to provide a user with a way to hang a package in an easy and convenient way. A first version of the present invention involves a flexible packaging bag for containing a plurality of disposable absorbent articles. The flexible packaging bag includes a plurality of walls defining an interior space, a plurality of disposable absorbent articles contained in the interior space, a hanger, and an opener. The opener is adapted to allow access to the interior space. The opener defines a first condition and a second condition, wherein the plurality of disposable absorbent articles and the hanger are inaccessible in the first condition and the plurality of disposable absorbent articles and the hanger are accessible in the second condition Another version of the present invention relates to a method of hanging a package containing absorbent articles including providing the package having a first closed position wherein the absorbent articles are inaccessible, and an opener. The method further includes opening the package by the opener, thereby exposing a hanger and the absorbent articles, and hanging the package by the hanger.

A third version of the present invention relates to a method of providing a usage system for a flexible packaging bag including providing at least one flexible packaging bag according to version one from above, and providing instructions directing a user to open the flexible packaging bag to expose the hanger.

It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles of the invention. Together with the description, the drawings serve to explain various aspects of the invention.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings wherein:

FIG. 1 illustrates a disposable absorbent article, and more specifically a diaper (30), in which the term "disposable" means that the diaper (30) is designed to be used until soiled and then discarded, rather than being washed and being reused again. Examples of other suitable disposable absorbent articles that can be used with the flexible packaging bag of the present invention include, but are not limited to, disposable absorbent pants, training pants, feminine care products, incontinence products, disposable apparel, or the like. Hereafter, when used with reference to, by way of example, a diaper, the term "component" can refer, but is not limited, to all or a segment of a designated selected region, such as edges, corners, sides or the like; structural members such as elastic strips, absorbent pads, elastic layers or panels, layers of material, or the like; or a graphic. The term "graphic" can refer, but is not limited, to an image, design, pattern, symbology, indicia, or the like.

Figure 1:
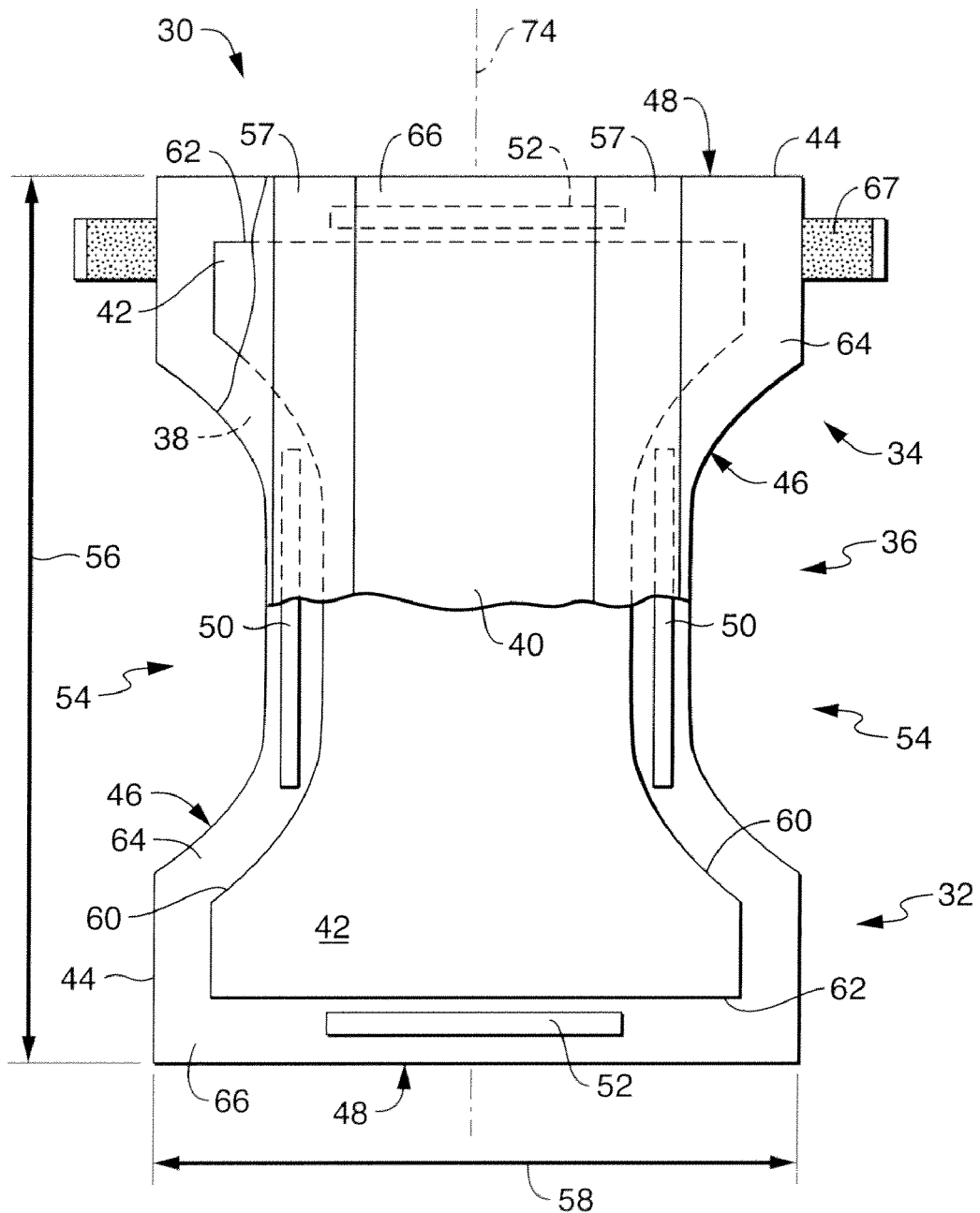
FIG. 1 illustrates a plan view of a disposable absorbent article in an unfolded, flat-out, uncontracted state (i.e., with all elastic induced gathering and contraction removed)

A disposable absorbent article, such as the diaper (30) illustrated in FIG. 1, can have multiple appearance-related and/or function-related components. Examples of components that are appearance-related include, but are not limited to, graphics; the highlighting or emphasizing of leg and waist openings in order to make product shaping more evident or visible; the highlighting or emphasizing of areas of the article to simulate functional components such as elastic leg bands, elastic waistbands, the highlighting of areas of the product to change the appearance of the size of the product; selectively positioned wetness indicators; back labels or front labels; and selectively positioned written instructions at a desired location on the article.

Examples of functional components include, but are not limited to, waist elastics, leg elastics, areas of breathability, fluid repellent areas, fluid wettable areas, adhesives, coatings, encapsulated inks, chemically-sensitive materials, environmentally-sensitive materials, heat-sensitive materials, moisture-sensitive materials, perfumes, odor control agents, inks, fasteners, fluid storage areas, textured or embossed areas, or the like.

The diaper (30) is shown in FIG. 1 in an unfolded, flat-out, uncontracted state (i.e., with all elastic induced gathering and contraction removed). Portions of the structure are partially cut away to more clearly show the interior construction of the diaper (30), with the surface of the diaper (30) which contacts the wearer facing the viewer.

FIG. 1 illustrates a disposable diaper (30) as having a front region (32), a rear region (34) and a crotch region (36) located between the front and rear regions. The diaper (30) comprises a backsheet (38), a topsheet (40), and an absorbent core (42) situated between the backsheet and the topsheet. The outer edges of the diaper (30) define a periphery (44) with transversely opposed, longitudinally extending side edges (46); longitudinally opposed, transversely extending end edges (48); and a system of elastomeric gathering members, such as a system including leg elastics (50) and waist elastics (52). The longitudinal side edges (46) define the leg openings (54) for the diaper (30), and optionally, are curvilinear and contoured. The transverse end edges (48) are illustrated as straight, but optionally, may be curvilinear. The diaper (30) may also comprise additional components to assist in the acquisition, distribution and storage of bodily waste. For example, the diaper (30) may comprise a transport layer, such as described in U.S. Pat. No. 4,798,603, issued to Meyer et al., or a surge management layer, such as described in European Patent Application Publication No. 0 539 703, published May 5, 1993.

The diaper (30) generally defines a longitudinally extending length dimension (56), and a laterally extending width dimension (58), as representatively illustrated in FIG. 1. The diaper (30) may have any desired shape, such as rectangular, I-shaped, a generally hourglass shape, or a T-shape.

The backsheet (38) defines a length and a width that, in the illustrated version, coincide with the length and width of the diaper (30). The absorbent core (42) generally defines a length and width that are less than the length and width of the backsheet (38), respectively. Thus, marginal portions of the diaper (30), such as marginal sections of the backsheet (38), may extend past the transversely opposed, longitudinally extending terminal side edges (60) and/or the longitudinally opposed, transversely extending terminal end edges (62) of the absorbent core (42) to form side margins (64) and end margins (66) of the diaper (30). The topsheet (40) is generally coextensive with the backsheet (38), but may optionally cover an area that is larger or smaller than the area of the backsheet, as desired. The backsheet (38) and topsheet (40) are intended to face the garment and body of the wearer, respectively, while in use. As used herein when describing the topsheet (40) in relation to the backsheet (38) and vice versa, the term "associated" encompasses configurations in which the topsheet is directly joined to the backsheet, and configurations where the topsheet is indirectly joined to the backsheet by affixing portions of the topsheet to intermediate members which in turn are affixed to at least portions of the backsheet. The topsheet (40) and the backsheet (38) can, for example, be joined to each other in at least a portion of the diaper periphery (44) by attachment mechanisms (not shown) such as adhesive bonds, sonic bonds, thermal bonds, pinning, stitching, or a variety of other attachment techniques known in the art, as well as combinations thereof.

The topsheet (40) suitably presents a bodyfacing surface which is compliant, soft feeling, and non-irritating to the wearer's skin. Further, the topsheet (40) may be less hydrophilic than the absorbent core (42), to present a relatively dry surface to the wearer, and is sufficiently porous to be liquid permeable, permitting liquid to penetrate readily through its thickness. A suitable topsheet (40) may be manufactured from a wide selection of web materials, such as porous foams, reticulated foams, apertured plastic films, natural fibers, synthetic fibers (for example, polyester or polypropylene fibers), or a combination of natural and synthetic fibers. The topsheet (40) is suitably employed to help isolate the wearer's skin from liquids held in the absorbent core (42).

Various woven and nonwoven fabrics may be used for the topsheet (40). For example, the topsheet (40) may be composed of a meltblown or spunbonded web of polyolefin fibers. The topsheet (40) may also be a bonded-carded web composed of natural and/or synthetic fibers. The topsheet (40) may be composed of a substantially hydrophobic material, and the hydrophobic material may, optionally, be treated with a surfactant, or otherwise processed, to impart a desired level of wettability and hydrophilicity. Specifically, the topsheet (40) may be a nonwoven, spunbond, polypropylene fabric composed of about 2.8 to about 3.2 denier fibers formed into a web having a basis weight of about 22 gsm and a density of about 0.06 g/cc.

By way of illustration only, the topsheet (40) may also be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and comprises a blend of hydrogenated ethoxylated castor oil and sorbitan monooleate in a 55:45 weight ratio. The GLUCOPON 220UP surfactant is purchased from Henkel Corporation, Gulph Mills, Pa., and comprises alkyl polyglycoside. The surfactant may also include additional ingredients such as aloe. The surfactant may be applied by any conventional means, such as spraying, printing, brush coating, foam or the like. The surfactant may be applied to the entire topsheet (40) or may be selectively applied to particular sections of the topsheet, such as the medial section along the longitudinal centerline of a diaper, to provide greater wettability of such sections.

The backsheet (38) may suitably be composed of a material which is either liquid permeable or liquid impermeable. It is generally desirable that the backsheet (38) be formed from a substantially liquid impermeable material. For example, a typical backsheet (38) can be manufactured from a thin plastic film or other flexible liquid impermeable material. Moreover, the backsheet (38) may be formed from a polyethylene film having a thickness of from about 0.012 mm (0.5 mil) to about 0.051 mm (2.0 mils). If desirous of presenting the backsheet (38) with a more cloth-like feel, the backsheet may comprise a polyethylene film having laminated to the lower or opposing surface thereof a nonwoven web, such as a spunbond web of polyolefin fibers. For example, a polyethylene film having a thickness of about 0.015 mm (0.6 mil) may have thermally laminated thereto a spunbond web of polyolefin fibers, which fibers have a thickness of about 1.5 to about 2.5 denier per filament, which nonwoven web has a basis weight of about 24 gsm (0.7 osy). Methods of forming such cloth-like outer covers are known to those skilled in the art. Further the backsheet (38) may be a stretchable material, a method of forming such a material may be found in U.S. Pat. No. 5,226, 992 issued to Morman, further various examples of extensible materials are described in U.S. Pat. No. 6,264,641 issued to VanGompel et al.; the entire disclosures of which are hereby incorporated by reference in a manner that is consistent herewith Further, the backsheet (38) may be formed of a woven or nonwoven fibrous web layer which has been totally or partially constructed or treated to impart a desired level of liquid impermeability to selected regions that are adjacent or proximate the absorbent core (42). Still further, the backsheet (38) may optionally be composed of micro-porous "breathable" material that permits vapors to escape from the absorbent core (42) while still preventing liquid exudates from passing through the backsheet.

The absorbent core (42) may comprise a matrix of hydrophilic fibers, such as a web of cellulosic fluff, mixed with particles of a high-absorbency material commonly known as superabsorbent material. In a particular version, the absorbent core (42) comprises a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed.

The absorbent core (42) may have any of a number of shapes. For example, the absorbent core (42) may be rectangular, 1-shaped or T-shaped. It is often considered as desirable for the absorbent core (42) to be narrower in the crotch portion than the rear or front region(s).

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can comprise, for example, physical entanglement, crystalline domains, covalent bonds, ionic complexes and associations, hydrophilic associations, such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful. Processes for preparing synthetic, absorbent gelling polymers are disclosed in U.S. Pat. No. 4,076,663, issued to Masuda et al., and U.S. Pat. No. 4,286,082, issued to Tsubakimoto et al.

The high-absorbency material may be in a variety of geometric forms. It is desired that the high-absorbency material be in the form of discrete particles. However, the high-absorbency material may also be in the form of fibers, flakes, rods, spheres, needles, or the like. Often, the high-absorbency material is present in the absorbent core (42) in an amount of from about 5 to about 100 weight percent based on total weight of the absorbent core.

As representatively illustrated in FIG. 1, the diaper (30) may include a pair of containment flaps (57) that are configured to provide a barrier to the lateral flow of body exudates. The containment flaps (57) may be located along the longitudinally extending side edges (46) of the diaper (30) adjacent the side edges of the absorbent core (42). Each containment flap (57) typically defines an unattached edge that is configured to maintain an upright, perpendicular configuration in at least the crotch region (36) of the diaper (30) to form a seal against the wearer's body. The containment flaps (57) may extend longitudinally along the entire length of the absorbent core (42) or may only extend partially along the length of the absorbent core (42). When the containment flaps (57) are shorter in length than the absorbent core (42), the containment flaps (57) can be selectively positioned anywhere along the side edges (46) of the diaper (30) in the crotch region (36). The containment flaps (57) may extend along the entire length of the absorbent core (42) to better contain the body exudates.

The diaper (30) may further include elastics at the end edges (48) and side edges (46) of the diaper (30) to further prevent leakage of body exudates and support the absorbent core (42). For example, the diaper (30) may include a pair of leg elastics (50) that are connected to the side edges (46) of the diaper (30) crotch region (36). The diaper (30) may also include a pair of waist elastics (52) that are connected to the end edges (48) of the diaper (30). The leg elastics (50) and waist elastics (52) are generally adapted to fit about the legs and waist of a wearer in use to maintain a positive, contacting relationship with the wearer to effectively reduce or eliminate the leakage of body exudates from the diaper (30).

The elastics may be adhered to the backsheet (38) in a stretched position, or they may be attached to the backsheet (38) while the backsheet (38) is pleated, such that elastic constrictive forces are imparted to the backsheet (38). The leg elastics (50) may also include such materials as polyurethane, synthetic and natural rubber. The waist elastics (52) may be formed by elastic strands attached to the backsheet (38) or they may be formed by attaching separate pieces of stretchable materials to the waist regions of the article.

The disposable absorbent articles can but need not necessarily comprise fasteners (67) for securing the absorbent article about the waist of the wearer. The illustrated versions of the diaper (30) comprise such fasteners (67). In at least one version, the fasteners (67) are situated in the rear region (34) of the diaper (30), and are located inboard each longitudinal extending side edge (46). The fasteners (67) may be configured to encircle the hips of the wearer and engage the backsheet (38) of the front region (32) of the diaper (30) for holding the diaper (30) on the wearer. Suitable fasteners are well known to those of skill in the art and can comprise adhesive tape tab fasteners, hook and loop fasteners, mushroom fasteners, snaps, pins, belts and the like, and combinations thereof. Desirably, the fasteners (67) are releasably engageable directly with the garment-facing surface of the backsheet (38). Desirably, the fasteners (67) comprise a mechanical fastening system.

Figure 2:
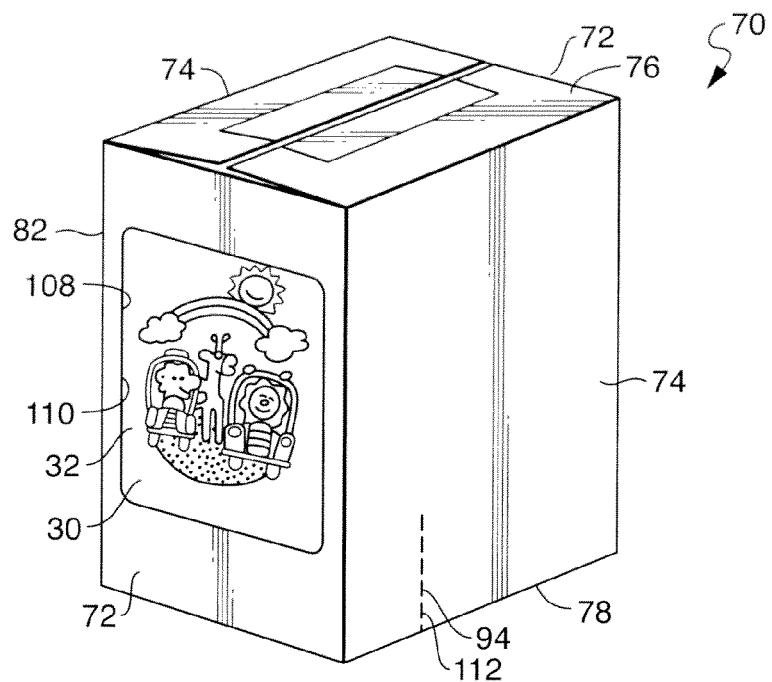
FIG. 2 illustrates a perspective view of a bag.
Figure 3:
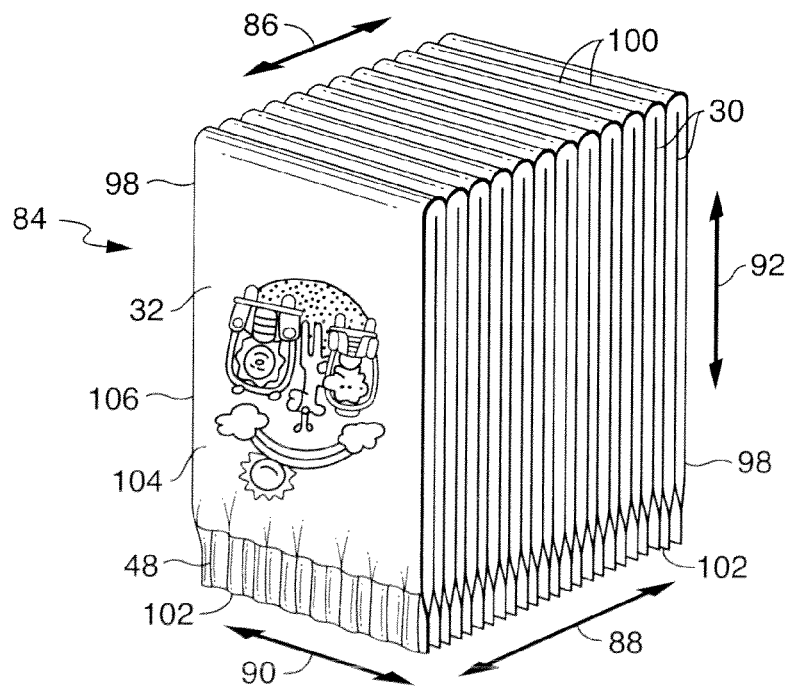
FIG. 3 illustrates a perspective view of a stack of articles.

Referring primarily to FIG. 2, there is illustrated a flexible packaging bag (70) having a polyhedral shape defining or forming a polyhedral enclosure. Specifically, bag (70) has a hexahedral shape that forms or defines a hexahedral enclosure. Bag (70) is defined by a plurality of walls, specifically a pair of end walls (72), a pair of side walls (74), a top wall (76), and a bottom wall (78). Each of the walls has a periphery, such as periphery (82) for an end wall (72). The walls (72), (74), (76), (78) define an interior space (80) (FIG. 4) for containing a stack (84) (FIG. 3) of articles, such as a plurality of diapers (30). In particular embodiments, the articles may be compressed in the bag (70). The term "compressed articles" or similar terminology will mean that the stack of articles, such as diapers (30) in FIG. 3, are compressed inwardly by a compression force at their front and back surfaces or panels, such as front region (32) and rear region (34), in a direction parallel to stack direction (86) (FIG. 3), so as to decrease the length dimension (88) of the originally, uncompressed articles. The compressed stack (84) also includes a width dimension (90) and a height dimension (92). The term "compression packed" or similar terminology describes the state or condition of diapers (30) after they have been compressed and inserted into bag (70). The term "expansion force" or similar terminology refers to that generally equal force exerted by the compressed stack (84) in a direction generally opposite and parallel to the compression force and against primarily end walls (72).

Bag (70) may be composed of a plurality of different materials, or may be composed of a single material. The material may be a polymer film which is sufficiently flexible to assume a desired, generally hexahedral shape when bag (70) is substantially filled with diapers (30). The material may be a nonwoven material. In addition, the material should have sufficient strength to hold and contain the diapers (30), or other articles, without breaking and without excessive bulging or stretching of the bag material. For example, the film material may be composed of a polyethylene film or film laminate having a thickness of about 2.5 mils (about 0.0635 millimeters). Other examples include a LDPE (low density polyethylene) film, a LDPE/LLDPE (linear low density polyethylene) film laminate, a LDPE/MDPE (medium density polyethylene) film laminate, a LDPE/HDPE (high density polyethylene) film laminate or the like. Naturally, the dimensions of bag (70) will depend upon the types of articles to be contained therein as well as the desired or aesthetically preferred shape. A suitable bag, and its method of construction, is illustrated and described in U.S. Pat. No. 5,282,687, the contents of which are incorporated by reference herein.

Figure 4:
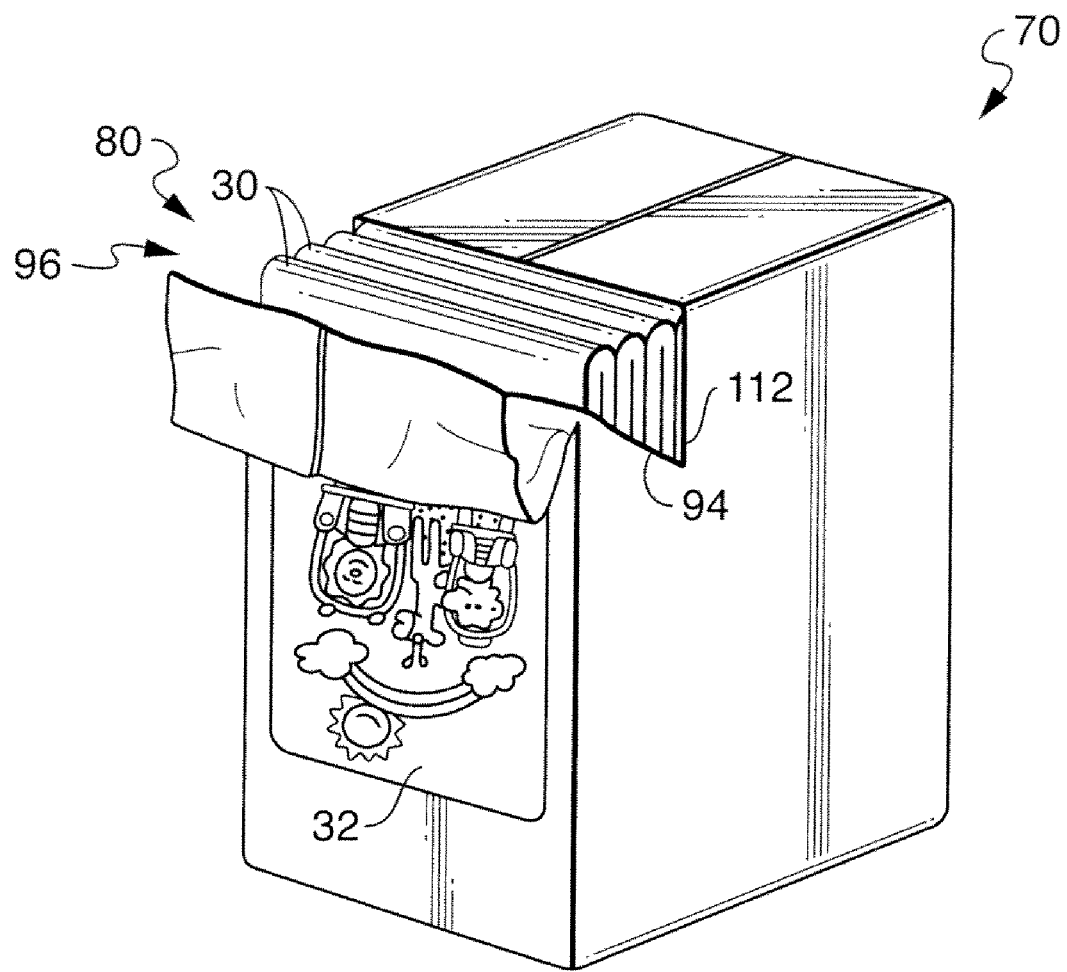
FIG. 4 illustrates a bag that has been opened to expose the interior space and the articles contained therein.

Bag (70) further includes an opener (112) for accessing the interior space (80) (FIG. 4) for dispensing the diapers (30) therefrom. The opener (112) may be a zipper, a removable tear strip, or a zip lock type seal. The opener (112) may be any device that is adapted to allow access to the interior space. The opener (112) may be a frangible line (94) that is easily broken, as shown in FIG. 2. A frangible line (94) can be disposed or manufactured at any position or location on bag (70) that would permit dispensing diapers (30) therefrom. As illustrated in FIG. 2, frangible line (94) is partially located in one side wall (74), continues underneath along bottom wall (78), and then upwardly along the opposite side wall (74) about the same distance as in the other side wall (74). This is also illustrated in FIG. 4 where frangible line (94) has been torn in order to provide an opening (96) for accessing and dispensing diapers (30). Frangible line (94) may, for example, be provided by partially cutting or otherwise thinning through the thickness of the bag material in a predetermined pattern, providing a selected pattern of perforations along the desired sections or walls of the bag, providing a desired pattern of stress-fatigue weakening along a desired line of the bag, or the like. As illustrated, frangible line (94) is provided by a line of perforations in which there can be approximately 2-10 perforations per lineal inch. The opener (112) may be located on a single wall of the bag; alternatively it may be located on a plurality of walls. Alternatively yet, the opener (112) may be located on an edge of a single or a plurality of walls.

Referring now primarily to FIG. 3, each diaper (30) has been folded such that the fasteners (67) are inwardly disposed between front region (32) and rear region (34). As illustrated in FIG. 3, each diaper (30) generally defines opposing side edges (98), a top edge (100), a bottom edge (102), opposing face surfaces (104) (only one of which is illustrated in FIG. 3), and a periphery (106). When the diapers (30) are compression packed in bag (70), surfaces (104) face along stack direction (86). Accordingly, the top edges (100) (as viewed in FIG. 3) of diapers (30) contact bottom wall (78), the bottom edges (102) of the diapers (30) contact the top wall (76) of bag (70), the side edges (98) of the diapers (30) contact the bag side walls (74), and the outermost face surface (104) of the end diaper (30) contacts end walls (72). Note that the bottom edge (102) of a diaper (30) in FIG. 3 corresponds to the end edges (48) (FIG. 1).

With reference primarily to FIGS. 2 and 4, bag (70) is opened by breaking frangible line (94) to gain access via opening (96) to diapers (30). Typically, the separation of frangible line (94) is initiated by breaking a portion thereof, and then propagating the break or tear along frangible line (94) through bottom wall (78) and those portions of side walls (74) into which frangible line (94) is manufactured. By thus breaking frangible line (94), the user can insert a finger or thumb through opening (96) in order to gain access to diaper (30). Thereafter, the user can grasp the top of a diaper (30) and pull it out of bag (70), while the remaining diapers (30) are maintained within the confines or interior space (80).

Referring primarily to FIG. 2, bag (70) may further include a window (108) disposed or positioned within a portion of end wall (72). Window (108) includes a window periphery (110) that has a shape that is substantially similar to the periphery of end wall (72). Window (108) at least substantially frames a component of the diapers (30) contained within bag (70). A suitable bag, and its method of construction, are illustrated and described in U.S. Pat. No. 6,491,165, the contents of which are incorporated by reference herein.

Depending upon the type of articles to be contained in bag (70), and the components, such as graphics, of those articles, it may be desirable to have a window in a different wall from end walls (72). For example, should a stack of articles be packaged in a different orientation in bag (70), then one of the side walls (74), or the top wall (76) or the bottom wall (78), can have a window to permit a component to be visually perceived therethrough.

The life cycle of the bag (70) of diapers (30) contains several unique phases. The first phase consists of manufacture and shipping to a retailer. In this phase, a primary function of the bag (70) is to contain and protect the diapers (30) from the environment. Further, in this stage, any extra pieces located on the exterior of the bag (70) may cause difficulties in shipping, handling and stacking of the bag (70). It is desired for the bag to have a minimal amount of these extra pieces on the exterior of the bag (70). The second phase of the life cycle of the bag (70) of diapers (30) consists of display on a retailer's shelf, purchase, and transport to the user point of use. In this second phase, the bag still contains and protects the diapers (30) but it may also be desirous for the bag (70) to inform the user about the contents of the bag (70). The third phase of the life cycle of the bag (70) of diapers (30) consists of the opening and use of individual diapers (30) one by one. This third phase, specifically the opening and dispensing presents the user with unique challenges which the present invention addresses.

Referring now to FIGS. 5A, 5B, 6A, 6B, 7A, 7B, 8A and 8B, the status of opener (112) defines a first condition (114) and a second condition (116). In the first condition (114) the bag (70) contains the diapers (30) and a hanger (118). In the first condition the diapers (30) and the hanger (118) are inaccessible. For purposes of this invention, inaccessible refers to a condition where there are no openings in the bag (70) large enough to permit the removal and use of either the diapers (30) or the hanger (118). In the second condition (116) the opener (112) has been activated to form an opening (96) though which the diapers may be removed. Further, in the second condition the hanger (118) also is accessible. For purposes of this invention, accessible refers to a condition where there are openings in the bag (70) large enough to permit the removal and use of the diapers (30) or the hanger (118). The hanger (118) may be used by the consumers in any number of ways. The hanger (118) may be used to hang the bag (70) on a changing table or from a hook, or any number of locations that may be useful to the consumer. Instruction regarding the use of the bag (70), opener (112) and hanger (118) may be provided on the exterior of the bag (70) or any other suitable form.

Figure 5A:
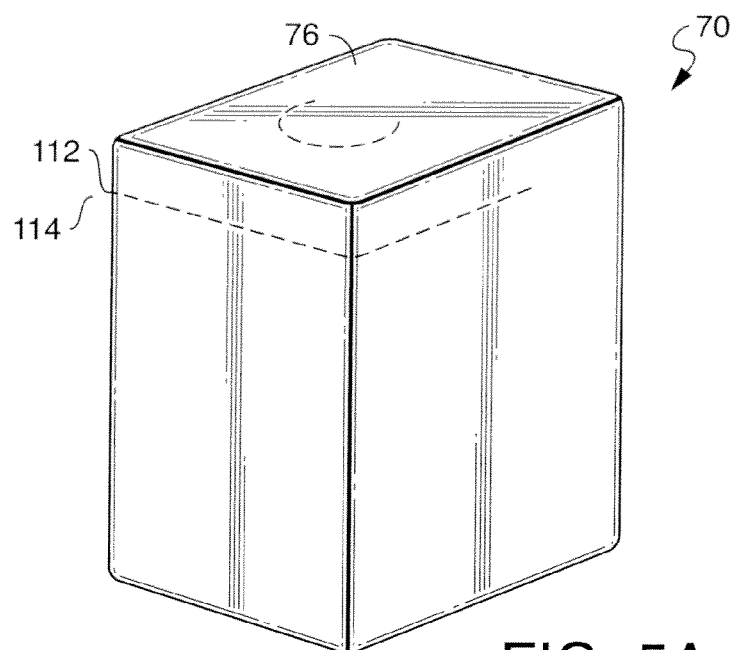
FIG. 5A illustrates a bag in a first condition.
Figure 5B:
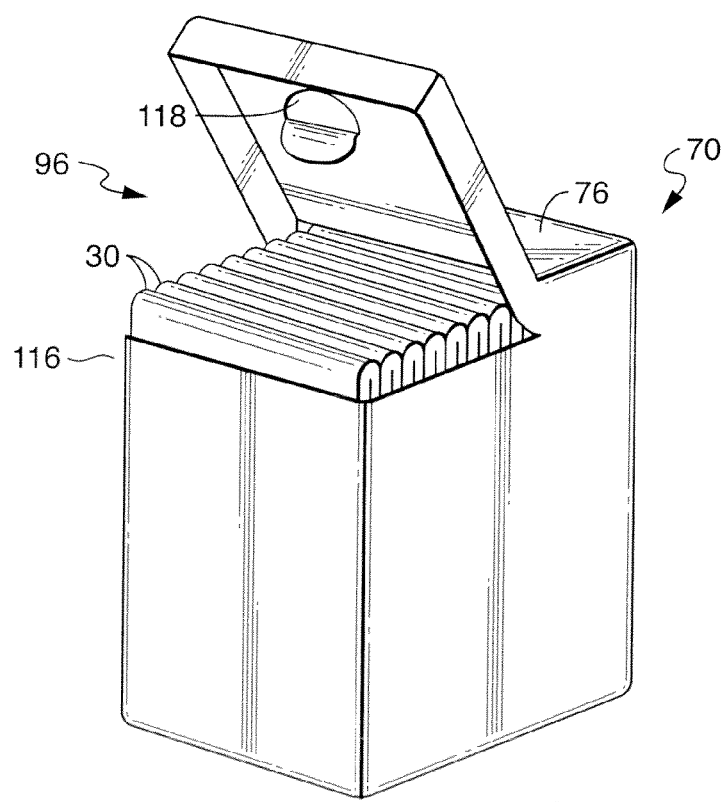
FIG. 5B illustrates the bag from FIG. 5A in a second condition.

The hanger (118) may take any number of forms. As shown in FIGS. 5A and 5B, the hanger (118) may be an opening in one of the walls formed by perforations. As shown in FIGS. 5A and 5B, the hanger (118) is an opening in the top wall (76) positioned such that when the bag (70) is in the second condition (116) with the diapers (30) accessible, the hanger (118) may then be activated and be used to hang the bag (70).

Figure 6A:
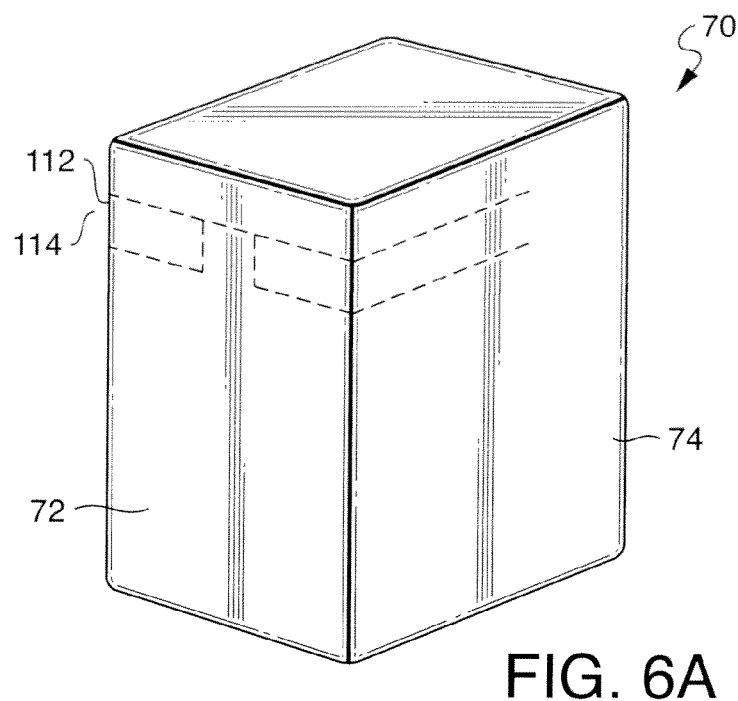
FIG. 6A illustrates a second bag in a first condition.
Figure 6B:
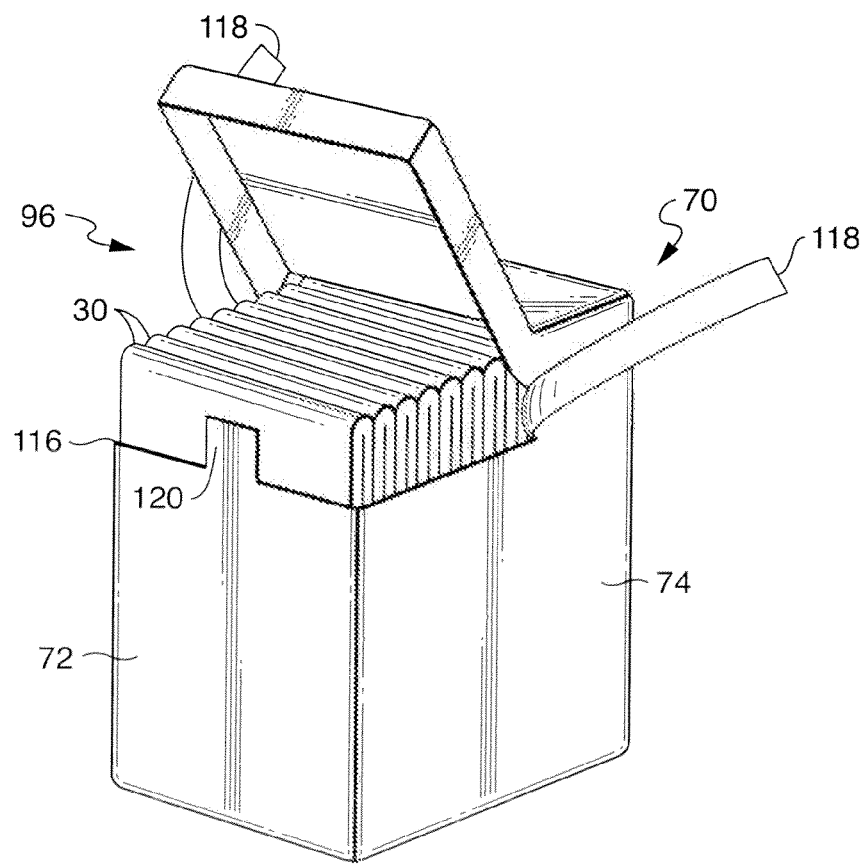
FIG. 6B illustrates the bag from FIG. 6A in a second condition.

A second form that the hanger (118) may take is shown in FIGS. 6A and 6B. As above, the bag (70) has a first condition (114) (shown in FIG. 6A) and a second condition (116) (shown in FIG. 6B). The hanger (118) is formed from portions of an end wall (72) and side walls (74). Specifically, perforations in the end and side walls (72, 74) may be torn to access the hanger (118) which then comprises two ties. These ties may then be used to hang the bag (70). This may be an economical way to provide a hanger (118) on a bag (70).

Figure 7A:
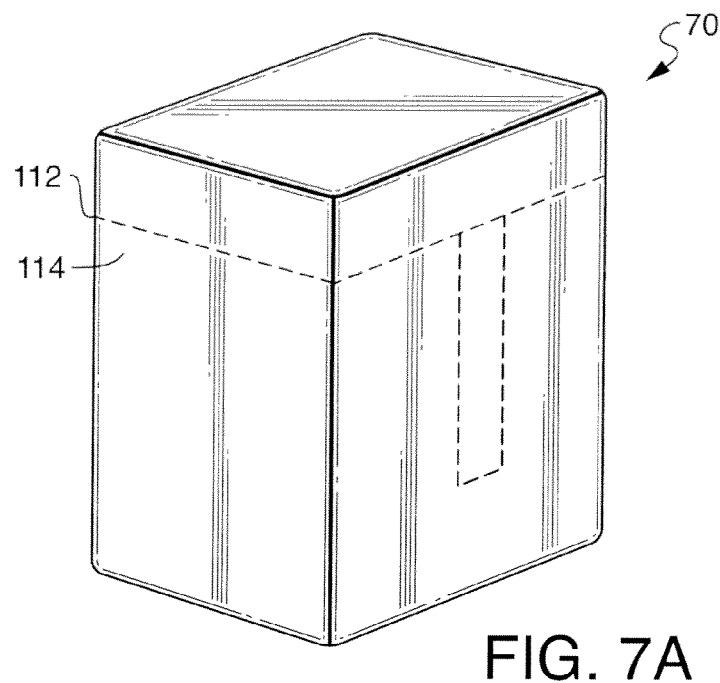
FIG. 7A illustrates a third bag in a first condition.
Figure 7B:
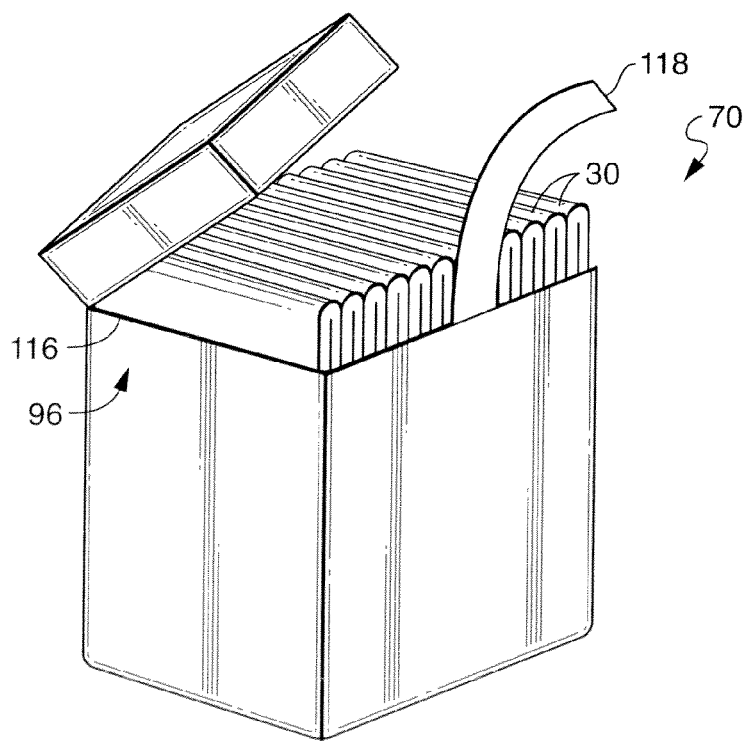
FIG. 7B illustrates the bag from FIG. 7A in a second condition.

FIGS. 7A and 7B illustrate a third bag (70) with a hanger (118). The hanger (118) comprises a tie which is located in the interior space (80) of the bag (70). When the bag (70) is in the first condition (114) the hanger (118) is inaccessible; however, when the bag (70) is in the second condition (116), a portion of the hanger (118) may be removed from the interior space (80) and be used to hang the bag. The hanger (118) may comprise a portion of a material which comprises one or more of the walls (72, 74, 76, 78) or the hanger may comprise a piece or pieces of material connected, either directly or indirectly, to an interior surface of the bag (70).

Figure 8A:
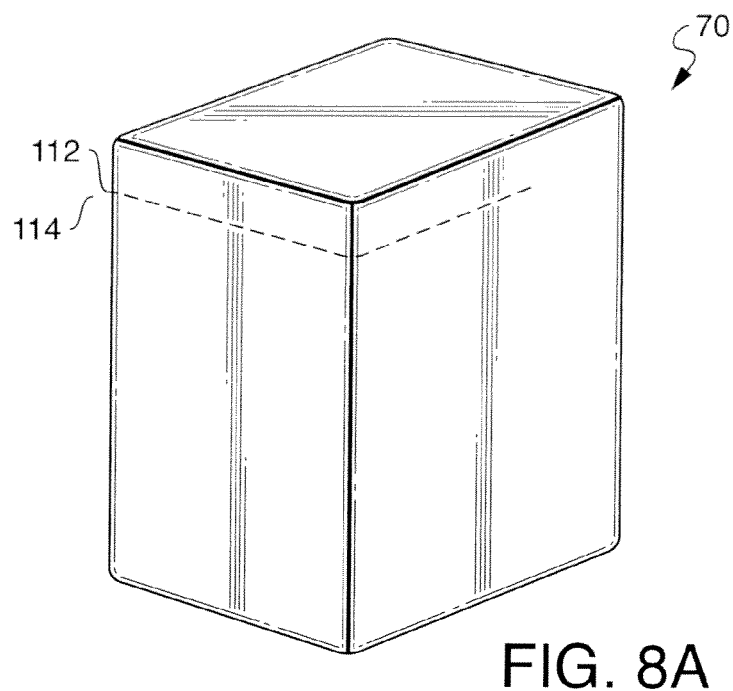
FIG. 8A illustrates a fourth bag in a first condition.
Figure 8B:
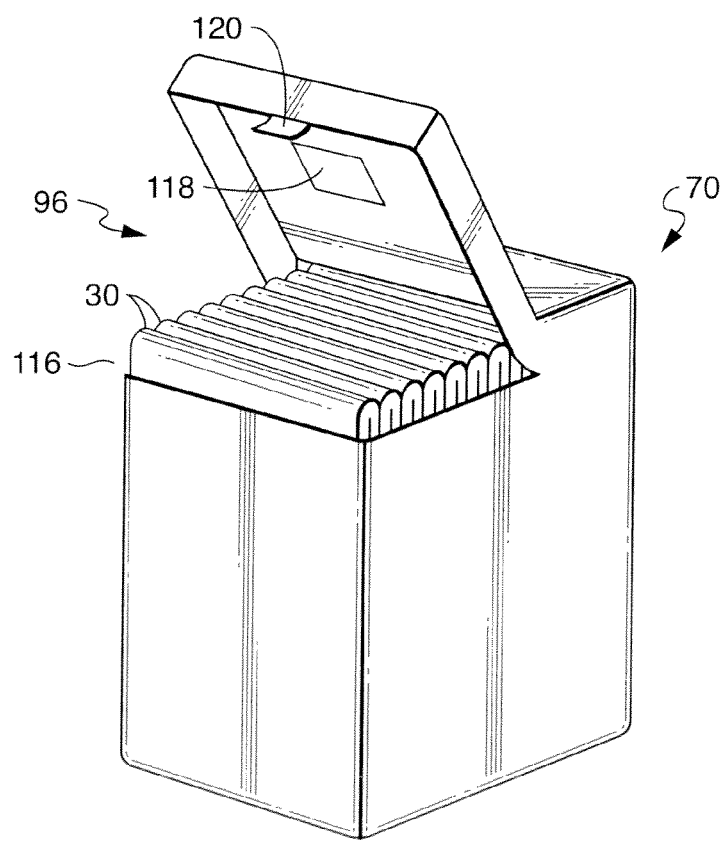
FIG. 8B illustrates the bag from FIG. 8A in a second condition.

FIGS. 8A and 8B illustrate a fourth bag (70) with a hanger (118). The hanger (118) is a fastener which is located on an inner surface of the bag (70). When the bag (70) is in the first condition (114) the hanger (118) is inaccessible; however, when the bag (70) is in the second condition (116), the hanger (118) is exposed and may be used to fasten the bag (70) to hang it. The hanger (118) as shown is a hook fastener which may be fastened to a corresponding loop fastener. The hanger (118) may be any mechanical fastener, including a snap, an adhesive patch, either with or without a removable cover. The hanger (118) may be attached to the inner surface of the bag (70) either directly or indirectly, in any manner as known in the art.

The bag (70) may further comprise a closing element (120), as shown in FIGS. 6B and 8B. The closing element (120) secures the bag (70) in a third condition. The closing element (120) may be used to close the bag (70) after it has been in the second condition. The closing element (120) secures the bag (70) such that the diapers are inaccessible with the closing element (120) engaged. The closing element (120) and the hanger (118) may be configured such that the hanger (118) is accessible in the third condition (shown in FIG. 6B). Alternatively, the closing element (120) and the hanger (118) may be configured such that the hanger (118) is inaccessible in the third condition (shown in FIG. 8B).

The closing element (120) may take on a number of different forms. The closing element (120) may be a tie, an adhesive, a mechanical fastener or other suitable element. The closing element may be different than the hanger (118), alternatively the closing element (120) and the hanger (118) may be similar, such as both being hook and loop type fasteners, both being snap fasteners, or both being ties. Alternatively, the closing element (120) and the hanger (118) may be identical.

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed is:

1. A flexible packaging bag for containing a plurality of disposable absorbent articles, the flexible packaging bag comprising:
    a plurality of walls defining an interior space,
    a plurality of disposable absorbent articles contained in and compression packed in the interior space,
    a hanger disposed within the interior space, and
    an opener adapted to allow access to the interior space, the opener defining a first condition and a second condition, wherein both the plurality of disposable absorbent articles and the hanger are inaccessible in the first condition, and wherein both the plurality of disposable absorbent articles and the hanger are accessible in the second condition,
    wherein the disposable absorbent articles are diapers,
    wherein the opener is a frangible line in at least one of the walls, and
    wherein the walls comprise a poly film.

2. The bag of claim 1 wherein the hanger comprises a mechanical fastener or a pair of ties.

3. The bag of claim 1 further comprising a closing element adapted to define a third condition, wherein the plurality of disposable absorbent articles are inaccessible in the third condition.

4. The bag of claim 3 wherein the hanger is accessible in the third condition.

5. The bag of claim 3 wherein the closing element and the hanger are similar.

6. A flexible packaging bag for containing a plurality of disposable absorbent articles, the flexible packaging bag comprising:
    a plurality of walls defining an interior surface and an interior space,
    a plurality of disposable absorbent articles contained in and compression packed in the interior space,
    a hanger disposed within the interior space, and
    an opener adapted to allow access to the interior space, the opener defining a first condition and a second condition, wherein the plurality of disposable absorbent articles and the hanger are inaccessible in the first condition and the plurality of disposable absorbent articles and the hanger are accessible in the second condition, wherein the hanger comprises a piece of material connected to the interior surface, a mechanical fastener, or an opening in one of the walls,
    wherein the disposable absorbent articles are diapers,
    wherein the opener is a frangible line in at least one of the walls, and
    wherein the walls comprise a poly film.

* * * * *